US012592079B2

(12) United States Patent
Suzuki et al.

(10) Patent No.: US 12,592,079 B2
(45) Date of Patent: Mar. 31, 2026

(54) PROGRAM, INFORMATION PROCESSING DEVICE, INFORMATION PROCESSING SYSTEM, AND INFORMATION PROCESSING METHOD

(71) Applicant: TERUMO KABUSHIKI KAISHA, Tokyo (JP)

(72) Inventors: Ayato Suzuki, Kanagawa (JP); Tomohiro Oka, Elkton, MD (US); Yosuke Itamochi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/769,701

(22) Filed: Jul. 11, 2024

(65) Prior Publication Data

US 2024/0362917 A1 Oct. 31, 2024

Related U.S. Application Data

(63) Continuation of application No. PCT/JP2023/007183, filed on Feb. 28, 2023.

(30) Foreign Application Priority Data

Mar. 29, 2022 (JP) ................................. 2022-054471

(51) Int. Cl.
*G06V 20/52* (2022.01)
*A61B 34/20* (2016.01)
(Continued)

(52) U.S. Cl.
CPC .............. *G06V 20/52* (2022.01); *A61B 34/20* (2016.02); *G06T 11/206* (2013.01); *G06V 10/40* (2022.01);
(Continued)

(58) Field of Classification Search
CPC ........ G06V 20/52; G06V 10/40; G06V 10/70; G06V 40/10; G06V 40/20; G06V 2201/03;
(Continued)

(56) References Cited

U.S. PATENT DOCUMENTS 6,909,793 B1 * 6/2005 Mori .................... G06V 10/245
382/128
9,351,641 B2 * 5/2016 Neff ...................... G06T 7/0012
(Continued)

FOREIGN PATENT DOCUMENTS

JP 2012183269 A 9/2012
JP 2014045239 A 3/2014
(Continued)

OTHER PUBLICATIONS

International Search Opinion, PCT/JP2023/007183, May 23, 2023.
International Search Report, PCT/JP2023/007183, May 23, 2023.

*Primary Examiner* — Brian P Yenke
(74) *Attorney, Agent, or Firm* — MacMillan, Sobanski & Todd, LLC

(57) ABSTRACT

A method, information processing device, and an information processing system are provided for automatically and accurately recording information about medical devices in an operating room. A surgical space image is captured by an imaging device, wherein the image includes monitor screens of a plurality of display devices dispersedly located in the surgical space. Measurement information is extracted from the monitor screen of each of the display devices on the basis of the acquired surgical space image. The extracted information regarding the monitor screen of each of the display devices is stored in time series to collectively manage the medical devices.

15 Claims, 15 Drawing Sheets

| TIME POINT | IMAGING DEVICE 10 | IMAGING DEVICE 11 | IMAGING DEVICE 12 |
|---|---|---|---|
| T1 | ○ | ○ | ○ |
| T2 | × | ○ | ○ |
| T3 | ○ | ○ | ○ |

(51) Int. Cl.

| | |
|---|---|
| *G06T 11/20* | (2006.01) |
| *G06V 10/40* | (2022.01) |
| *G06V 10/70* | (2022.01) |
| *G06V 40/20* | (2022.01) |
| *A61B 90/00* | (2016.01) |
| *G06V 40/10* | (2022.01) |

(52) U.S. Cl.
CPC .............. *G06V 10/70* (2022.01); *G06V 40/20* (2022.01); *A61B 2034/2065* (2016.02); *A61B 2090/372* (2016.02); *G06T 2207/30196* (2013.01); *G06T 2210/41* (2013.01); *G06V 40/10* (2022.01); *G06V 2201/02* (2022.01); *G06V 2201/03* (2022.01)

(58) Field of Classification Search
CPC .............. G06V 2201/02; G06T 11/206; G06T 2207/30196; G06T 2201/41; A61B 2090/372; A61B 2034/2065; A61B 34/20
See application file for complete search history.

(56)  References Cited

U.S. PATENT DOCUMENTS

| | | | | |
|---|---|---|---|---|
| 9,418,314 | B2 | 8/2016 | Nomura et al. | |
| 9,654,743 | B2 * | 5/2017 | Harada ................ | A61B 5/6898 |
| 11,133,104 | B2 * | 9/2021 | Esterberg ............. | G16H 40/20 |
| 11,357,582 | B1 * | 6/2022 | Roh ........................ | G16B 20/20 |
| 12,336,855 | B2 * | 6/2025 | Sun ........................ | A61B 6/547 |
| 2014/0098209 | A1 * | 4/2014 | Neff ...................... | A61B 5/742 |
| | | | | 348/77 |
| 2015/0182114 | A1 * | 7/2015 | Wang .................... | A61B 90/90 |
| | | | | 600/549 |
| 2018/0197018 | A1 * | 7/2018 | Nakasu ................. | G06V 40/16 |
| 2021/0043308 | A1 | 2/2021 | Sugie et al. | |
| 2021/0307864 | A1 * | 10/2021 | Wolf ..................... | G11B 27/34 |
| 2023/0162840 | A1 * | 5/2023 | Hosoya ................. | G16H 40/63 |
| | | | | 705/2 |

FOREIGN PATENT DOCUMENTS

| | | | |
|---|---|---|---|
| JP | 5601250 | B2 | 10/2014 |
| JP | 2015188566 | A | 11/2015 |

* cited by examiner

| IMAGING DATE AND TIME | SURGICAL SPACE IMAGE | MONITOR IMAGE | | | |
|---|---|---|---|---|---|
| | | MONITOR 201 | MONITOR 211 | MONITOR 221 | ... |
| 2021/12/1 10:30:00 | 000001. jpg | x1, y1, w1, h1 | x2, y2, w2, h2 | x3, y3, w3, h3 | ... |
| 2021/12/1 10:30:02 | 000002. jpg | x1, y1, w1, h1 | x2, y2, w2, h2 | x3, y3, w3, h3 | ... |
| 2021/12/1 10:30:04 | 000003. jpg | x1, y1, w1, h1 | x2, y2, w2, h2 | x3, y3, w3, h3 | |
| ... | ... | ... | ... | ... | ... |

| IMAGING DATE AND TIME | MEASUREMENT INFORMATION | | | |
|---|---|---|---|---|
| | MONITOR 201 | MONITOR 211 | MONITOR 221 | ··· |
| 2021/12/1　10:30:00 | 53 | 80 | 95 | ··· |
| 2021/12/1　10:30:02 | 55 | 82 | 96 | ··· |
| 2021/12/1　10:30:04 | 56 | 82 | 96 | ··· |
| ··· | ··· | ··· | ··· | ··· |

| TIME POINT | IMAGING DEVICE 10 | IMAGING DEVICE 11 | IMAGING DEVICE 12 |
|---|---|---|---|
| T1 | ○ | ○ | ○ |
| T2 | × | ○ | ○ |
| T3 | ○ | ○ | ○ |

FIG. 11
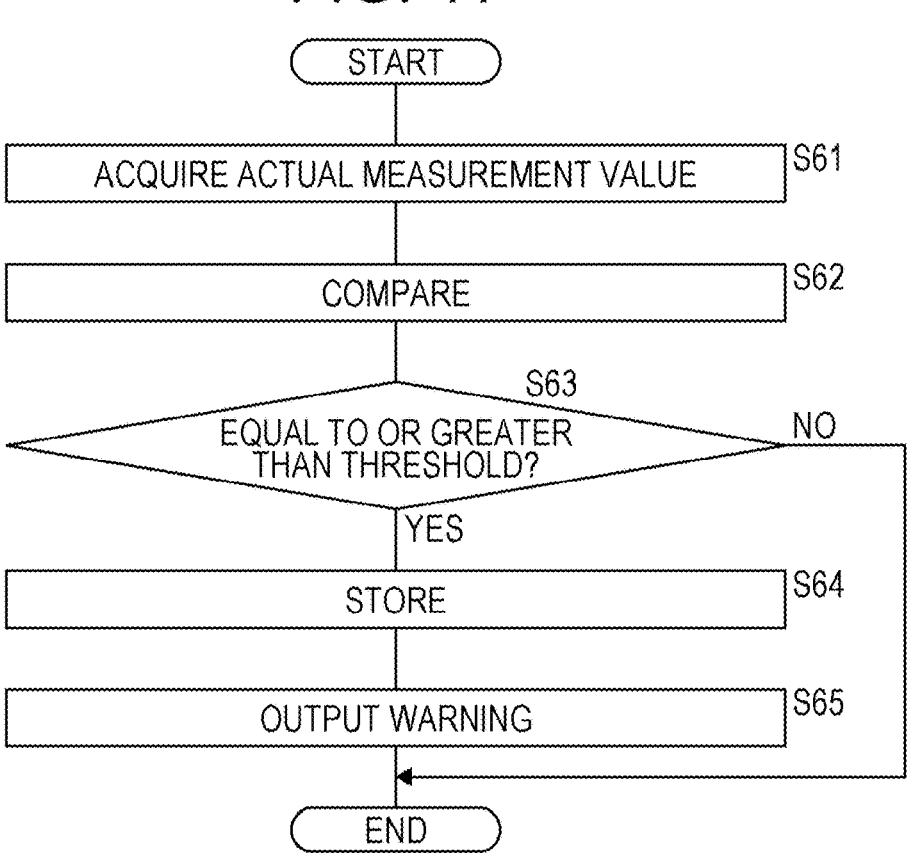
FIG. 12
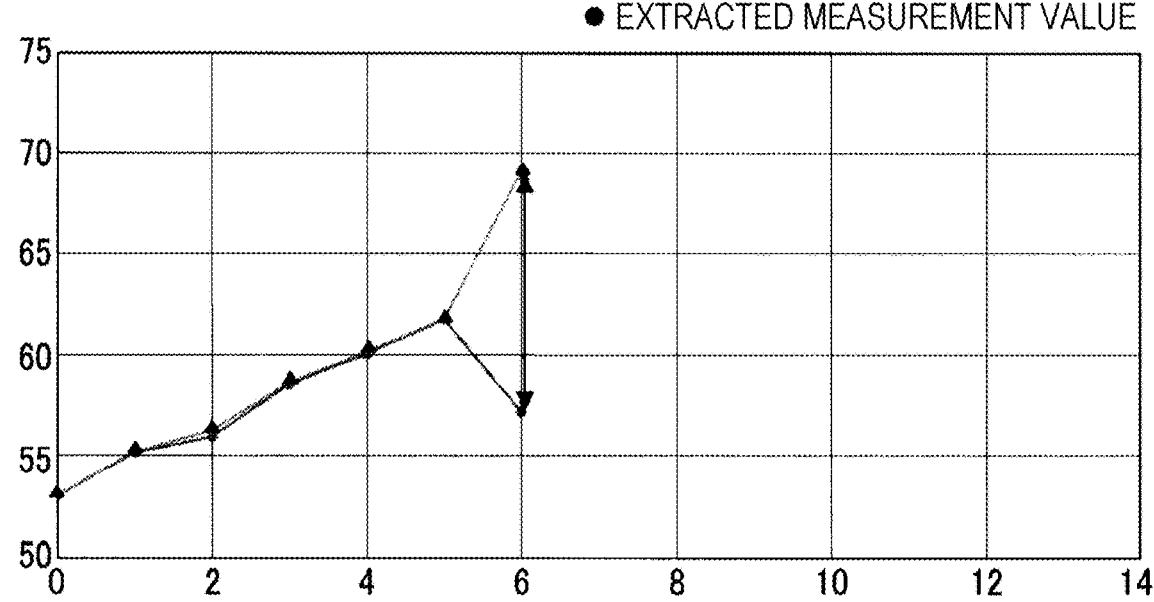

FIG. 13

▲ ACTUAL MEASUREMENT VALUE
● EXTRACTED MEASUREMENT VALUE

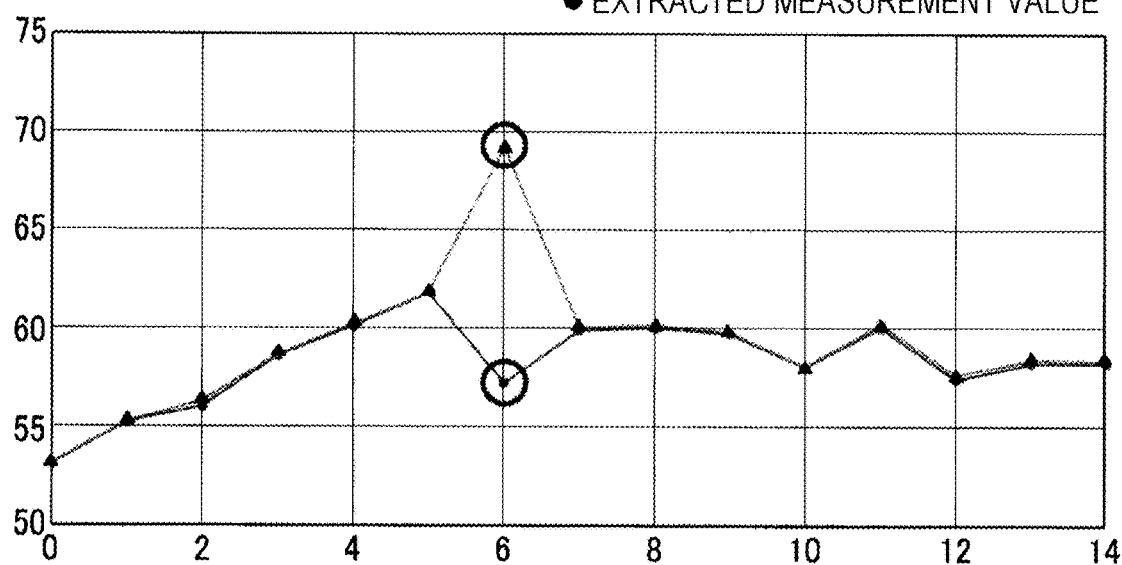

FIG. 14

| TYPE OF ABNORMALITY | MEASUREMENT ITEM | | | | ADVICE |
|---|---|---|---|---|---|
| | K1 | K2 | K3 | K4 | |
| ABNORMALITY A | ~2x | ~3x | ~x | ~x | THERE MAY BE THROMBUS IN CANNULA FOR DRAWING BLOOD |
| ABNORMALITY B | ~2x | +x | ~2x | ~2x | BEWARE OF PUMP ABNORMALITY |
| ABNORMALITY C | ~2x | +x | +2x | ~2x | THERE MAY BE THROMBUS IN ARTIFICIAL LUNG |
| ABNORMALITY D | ~2x | +x | +3x | +3x | THERE MAY BE THROMBUS IN CANNULA FOR DELIVERING BLOOD |

FIG. 18

| IMAGING DATE AND TIME | MEASUREMENT INFORMATION | | | | ABNORMALITY FLAG | BEHAVIOR OF OPERATOR | TYPE OF ABNORMALITY |
|---|---|---|---|---|---|---|---|
| | MONITOR 201 | MONITOR 211 | MONITOR 221 | ··· | | | |
| 2021/12/1 10:30:00 | 53 | 80 | 95 | ··· | 1 | ELECTRIC SCALPEL | NOISE |
| 2021/12/1 10:30:02 | 55 | 82 | 96 | ··· | 0 | WAITING | NONE |
| 2021/12/1 10:30:04 | 56 | 82 | 96 | ··· | 1 | OPERATE ECMO | PUMP FAILURE |
| ··· | ··· | ··· | ··· | ··· | ··· | ··· | ··· |

FIG. 19

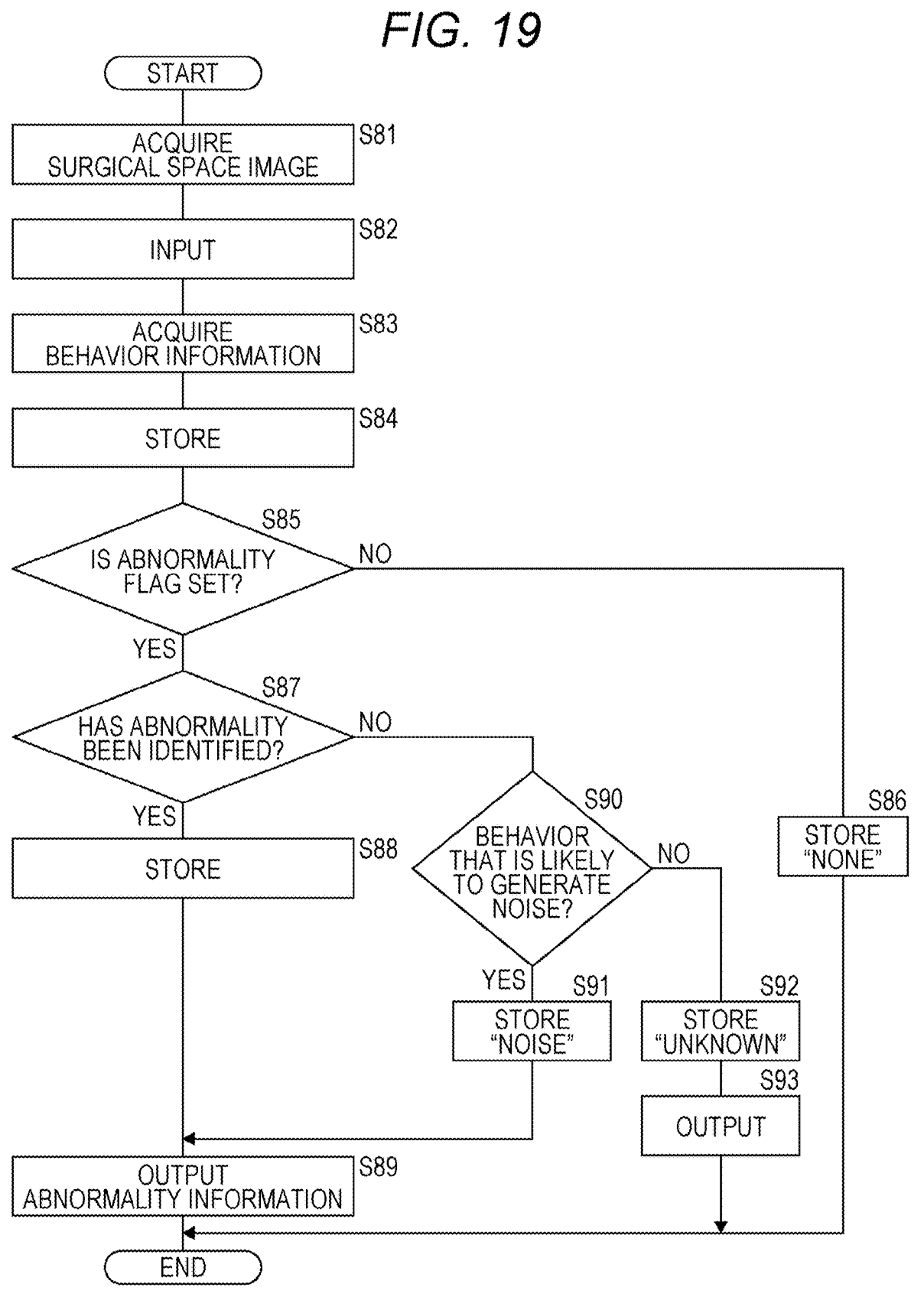

START

ACQUIRE SURGICAL SPACE IMAGE — S81

INPUT — S82

ACQUIRE BEHAVIOR INFORMATION — S83

STORE — S84

S85 — IS ABNORMALITY FLAG SET? — NO → S86 STORE "NONE"

YES

S87 — HAS ABNORMALITY BEEN IDENTIFIED? — NO → S90 BEHAVIOR THAT IS LIKELY TO GENERATE NOISE?

YES

STORE — S88

S90 BEHAVIOR THAT IS LIKELY TO GENERATE NOISE? — YES → S91 STORE "NOISE"

S90 — NO → S92 STORE "UNKNOWN"

S93 OUTPUT

OUTPUT ABNORMALITY INFORMATION — S89

END

1

PROGRAM, INFORMATION PROCESSING DEVICE, INFORMATION PROCESSING SYSTEM, AND INFORMATION PROCESSING METHOD

CROSS REFERENCE TO RELATED APPLICATIONS

This application is a continuation of PCT Application No. PCT/JP2023/007183, filed Feb. 28, 2023, based on and claiming priority to Japanese Application No. JP2022-054471, filed Mar. 29, 2022, both of which are incorporated herein by reference in their entirety.

BACKGROUND OF THE INVENTION

The present invention relates to a program, an information processing device, an information processing system, and an information processing method.

For health management (e.g., medical treatment such as surgical care), it is known that body data (for example, body weight, body temperature, blood pressure, and the like) of an individual measured using a measuring device is accumulated in a server via a network and managed by the server. For example, an information processing device is disclosed which executes processing of storing numerical information acquired from an image displayed on a display unit of a body data measuring device for each type of measurement items of the body data measuring device (see, e.g., JP5601250B1).

However, it is difficult to automatically and accurately record information about various medical devices using the information processing device disclosed in JP5601250B1 in an operating room in which various medical devices are used for medical treatment.

In addition, there is a case where a plurality of measuring devices is used in an operating room, and the measuring devices are connected by cables to transfer data. At that time, erroneous recognition of data from each of the measuring devices due to cable noise generated in the cables may become a problem. Furthermore, since multiple cables are placed in the operating room, there is a concern of the risk of, for example, an operator stumbling while moving around in the operating room.

The present invention has been made in view of such circumstances, and an object thereof is to provide a program, an information processing device, an information processing system, and an information processing method with which it is possible to automatically and accurately record information about a medical device in an operating room.

SUMMARY OF THE INVENTION

A program according to one aspect of the present disclosure causes a computer to execute processing of: acquiring a surgical space image that is captured by an imaging device imaging a surgical space and that includes monitor screens of a plurality of display devices dispersedly located in the surgical space; extracting information regarding the monitor screen of each of the display devices on the basis of the acquired surgical space image; and storing the extracted information regarding the monitor screen of each of the display devices in time series.

An information processing device according to one aspect of the present disclosure includes: an acquisition unit that acquires a surgical space image which is captured by an imaging device imaging a surgical space and which includes monitor screens of a plurality of display devices dispersedly located in the surgical space; an extraction unit that extracts information regarding the monitor screen of each of the display devices on the basis of the surgical space image that has been acquired by the acquisition unit; and a storage unit that stores, in time series, the information regarding the monitor screen of each of the display devices that has been extracted by the extraction unit.

An information processing system according to one aspect of the present disclosure includes: an imaging device that acquires a surgical space image by imaging a surgical space, the surgical space image including monitor screens of a plurality of display devices dispersedly located in the surgical space; and an information processing device that communicates with the imaging device, wherein the information processing device includes an acquisition unit that acquires the surgical space image captured by the imaging device, an extraction unit that extracts information regarding the monitor screen of each of the display devices on the basis of the surgical space image that has been acquired by the acquisition unit, and a storage unit that stores, in time series, the information regarding the monitor screen of each of the display devices that has been extracted by the extraction unit.

An information processing method according to one aspect of the present disclosure is an information processing method executed by a computer, the method including steps of: acquiring a surgical space image which is captured by an imaging device imaging a surgical space and which includes monitor screens of a plurality of display devices dispersedly located in the surgical space; extracting information regarding the monitor screen of each of the display devices on the basis of the acquired surgical space image; and storing, in time series, the extracted information regarding the monitor screen of each of the display devices.

According to the present disclosure, information about medical devices in an operating room can be automatically and accurately recorded.

BRIEF DESCRIPTION OF THE DRAWINGS

FIG. 11 is a flowchart illustrating a procedure of information processing performed by a control unit of an information processing device according to the fourth embodiment.

FIG. 12 is a schematic diagram illustrating an example of information regarding an abnormality to be displayed on a display unit.

FIG. 13 is a schematic diagram illustrating an example of information regarding an abnormality to be displayed on a display unit.

FIG. 14 is a reference table for determining abnormality in an extracorporeal circulation device.

FIG. 18 is an explanatory diagram illustrating another example of a record layout in the measurement information DB.

FIG. 19 is a flowchart illustrating a procedure of information processing performed by a control unit of the information processing device according to the sixth embodiment.

DETAILED DESCRIPTION OF PREFERRED EMBODIMENTS

First Embodiment

Figure 1:
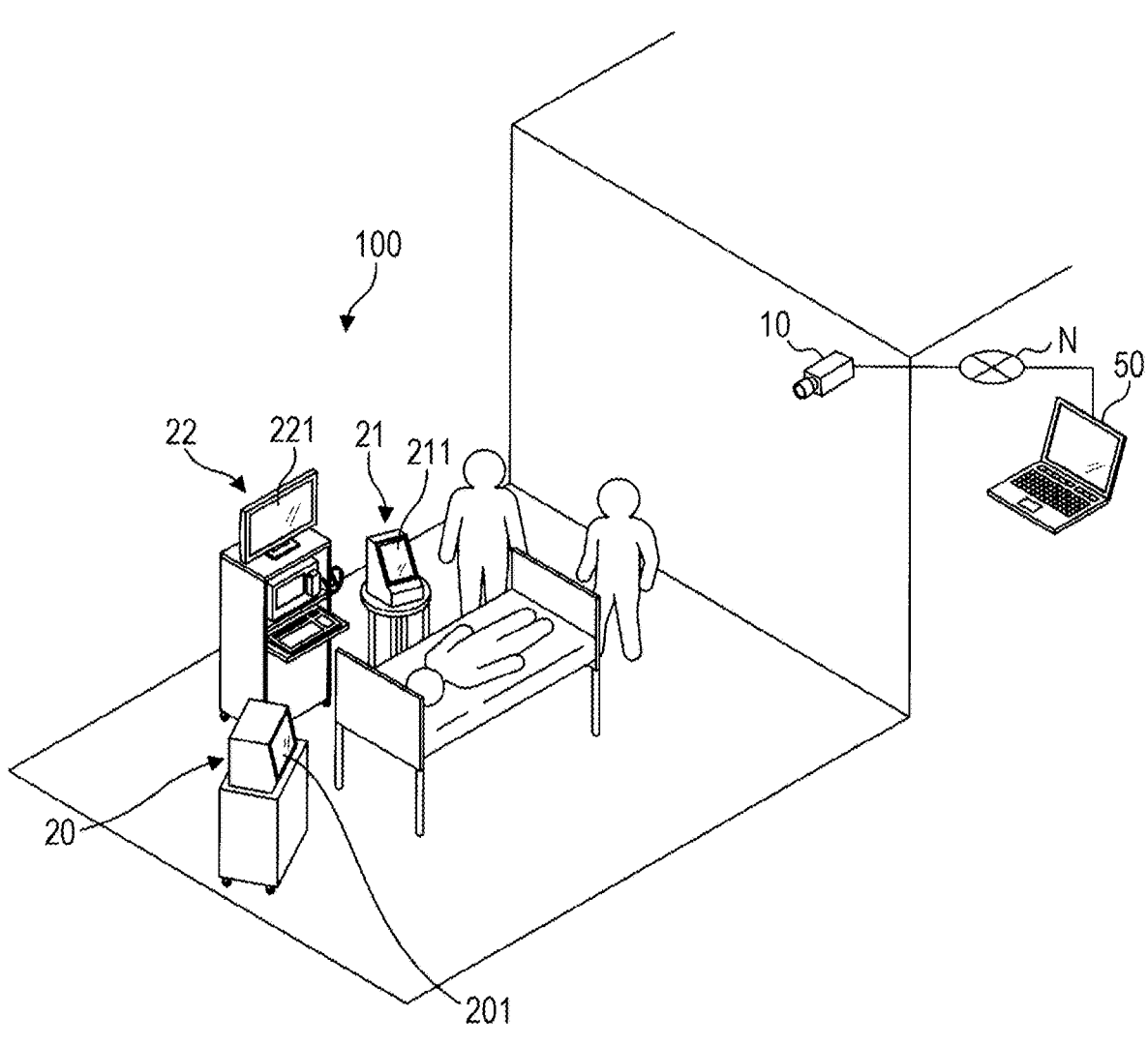
FIG. 1 is a schematic diagram for describing an overview of an information processing system according to a first embodiment.
Figures 2, 3:
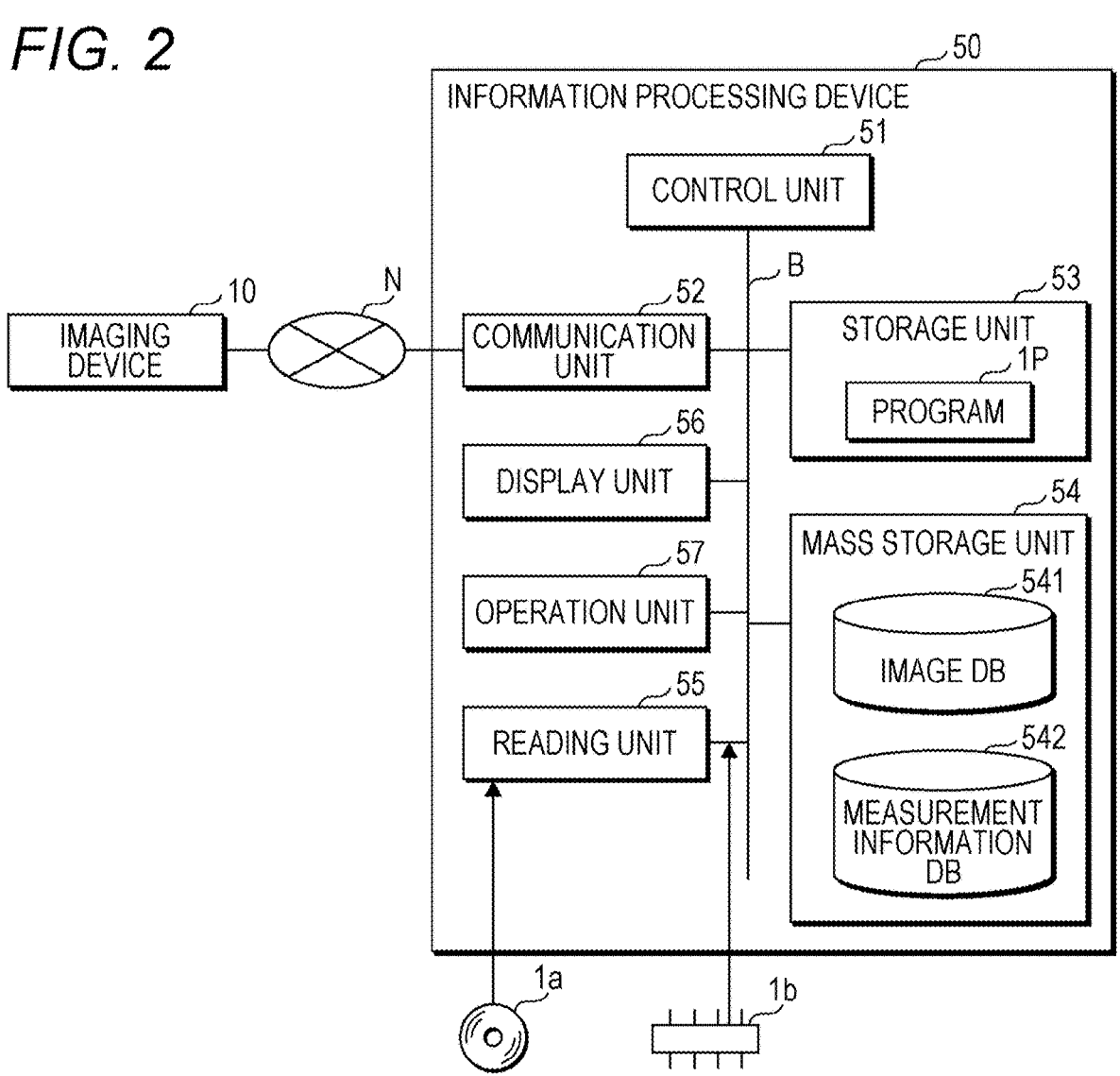
FIG. 2 is a block diagram illustrating an example of the configuration of the information processing system according to the first embodiment.
FIG. 3 is an explanatory diagram illustrating one example of a record layout in an image DB.

Hereinafter, embodiments of the present invention will be described with reference to the drawings. FIG. 1 is a schematic diagram for describing an overview of an information processing system according to a first embodiment. FIG. 2 is a block diagram illustrating an example of the configuration of the information processing system according to the first embodiment. The information processing system according to the first embodiment includes an imaging device 10 that captures an image of a surgical space in an operating room 100 in a hospital, and an information processing device 50 that communicates with the imaging device 10.

As illustrated in FIG. 1, a plurality of measurement devices 20, 21, 22, . . . for measuring biological information such as a pulse rate, arterial oxygen saturation, and a body temperature of a patient, for example, is installed in the operating room 100. Although three measurement devices are illustrated in FIG. 1, the number of measurement devices is not limited to three, and may be other than three. The measurement devices 20, 21, 22, . . . include monitors (display devices) 201, 211, 221, . . . that display measurement information, respectively. The monitors 201, 211, 221, . . . are dispersedly located in the operating room 100.

The imaging device 10 is, for example, a charge coupled device (CCD), a complementary metal oxide semiconductor (CMOS), or the like. The imaging device 10 captures an image of the surgical space in the operating room 100 at predetermined time intervals, for example, and transmits an image (hereinafter, referred to as a surgical space image) including display screens of a plurality of monitors 201, 211, 221, . . . obtained by the image capture to the information processing device 50. Note that the imaging device 10 may sequentially acquire the surgical space image of one frame by continuously imaging the surgical space in the operating room 100 during a surgery period. The imaging device 10 and the information processing device 50 are connected via a network N, but may be directly connected by a wired cable, or wirelessly connected using, for example, Bluetooth (registered trademark) to exchange information.

As shown in FIG. 2, the information processing device 50 includes a control unit 51 that controls the entire device, a communication unit 52, a storage unit 53, a mass storage unit 54, a reading unit 55, a display unit 56, and an operation unit 57. The respective components are connected by a bus B. In the first embodiment, the information processing device 50 is a personal computer, but the information processing device 50 may be a server device connected to the network N. Note that the information processing device 50 may be installed in the operating room 100 or may be installed in a place different from the operating room 100 (for example, a management room or the like).

The control unit 51 includes an arithmetic processing unit such as a central processing unit (CPU), a micro-processing unit (MPU), or a graphics processing unit (GPU) and executes various types of information processing, control processing, and the like performed by the information processing device 50 by reading and executing a program 1P for control stored in the storage unit 53. In FIG. 2, the control unit 51 is described as a single processor, but may be a multiprocessor.

The communication unit 52 is a communication module for performing processing related to communication, and transmits and receives information between the imaging device 10 and the information processing device 50 via the network N.

The storage unit 53 includes memory elements such as a random access memory (RAM) and a read only memory (ROM), and stores the program 1P, data, or the like necessary for the control unit 51 to execute processing. In addition, the storage unit 53 temporarily stores data and the like necessary for the control unit 51 to execute arithmetic processing.

The mass storage unit 54 includes a recording medium such as a hard disk drive (HDD) or a solid state drive (SSD). The mass storage unit 54 includes an image database (DB) 541 and a measurement information DB 542 to be described later.

In the present embodiment, the storage unit 53 and the mass storage unit 54 may be configured as an integrated storage device. In addition, the mass storage unit 54 may include a plurality of storage devices. Furthermore, the mass storage unit 54 may be an external storage device connected to the information processing device 50.

The reading unit 55 reads a portable storage medium 1a including a compact disc (CD)-ROM or a digital versatile disc (DVD)-ROM. The control unit 51 may read the program 1P from the portable storage medium 1a via the reading unit 55 and store the program 1P in the mass storage unit 54. In addition, the control unit 51 may download the program 1P from another computer via the network N or the like and store the program 1P in the mass storage unit 54. Furthermore, the control unit 51 may read the program 1P from a semiconductor memory 1b.

The display unit 56 is a liquid crystal display, an organic electroluminescence (EL) display, or the like, and displays various kinds of information in accordance with an instruction from the control unit 51. The operation unit 57 receives an operation from an operational personnel and notifies the control unit 51 of the received operation. The operation unit 57 receives an operation from the operational personnel by a mechanical button or an input device such as a touch panel provided on the surface of the display unit 56. Furthermore, the operation unit 57 may be an input device such as a mouse and a keyboard, and these input devices may be detachable from the information processing device 50.

The information processing device 50 according to the first embodiment acquires time-series surgical space images captured by the imaging device 10 via the communication unit 52, and the control unit 51 acquires the surgical space images, extracts information regarding the screens of the monitors 201, 211, 221, . . . on the basis of the acquired surgical space images, and stores the extracted information regarding the monitor screens in time series.

The control unit 51 extracts information regarding the monitor screen by, for example, executing detection processing of detecting the monitor screen and extraction processing of extracting measurement information displayed on the monitor screen to be described later on the surgical space image acquired via the communication unit 52. With respect to the detection processing of detecting the monitor screen, the control unit 51 detects the monitor screen from the surgical space image using, for example, a learning model trained in advance by machine learning. The learning model is trained in advance by machine learning to receive, for example, data of a surgical space image as an input and output region coordinates of a monitor screen included in the surgical space image. The learning model is trained by machine learning using, for example, training data in which the data of the surgical space image is associated with the coordinates indicating an image region, which includes the monitor screen, included in the surgical space image. The control unit 51 inputs the surgical space image captured by the imaging device 10 to the learning model and acquires the region coordinates of the monitor screen output by the learning model. Note that, regarding the processing of detecting the monitor screen, the control unit 51 may detect the monitor screen from the surgical space image captured by the imaging device 10 using, for example, a conventional object detection technology. The object detection technology is, for example, accelerated KAZE (A-KAZE), scale invariant feature transform (SIFT), or the like in addition to pattern matching, and detects a monitor screen by extracting a feature amount using a local feature amount extraction method. Furthermore, the storage unit 53 stores in advance a table in which, for each of the monitors 201, 211, 221, . . . , the frame shape of the monitor is associated with a measurement item to be displayed, and the control unit 51 can identify each of the monitors 201, 211, 221, . . . according to the frame shape of each of the monitors 201, 211, 221, . . . included in the surgical space image, and specify the measurement item. Note that the method for identifying each of the monitors 201, 211, 221, . . . is not limited to the above method, and for example, an identification marker (colored label or the like) may be attached in advance to each of the monitors 201, 211, 221, . . . , and the color of the marker and the measurement item may be associated with each other.

The control unit 51 stores the region coordinates of the monitor screen as data of the monitor image in the image DB 541 of the mass storage unit 54. The control unit 51 may extract an image region including the monitor screen from the surgical space image and store data of the extracted image region in the image DB 541 of the mass storage unit 54 as data of the monitor image. FIG. 3 is an explanatory diagram illustrating one example of a record layout in the image DB 541. As illustrated in FIG. 3, the image DB 541 includes an imaging date-and-time column, a surgical-space-image column, and a monitor image column. The imaging date-and-time column stores information about the imaging date and time of an image. The surgical-space-image column stores acquired surgical space images. The monitor image column stores region coordinates of the monitor screen indicated by four values that are an x coordinate, a y coordinate, a width (w), and a height (h). In addition, the monitor image column may store the extracted image of the monitor screen.

Figures 4, 5:
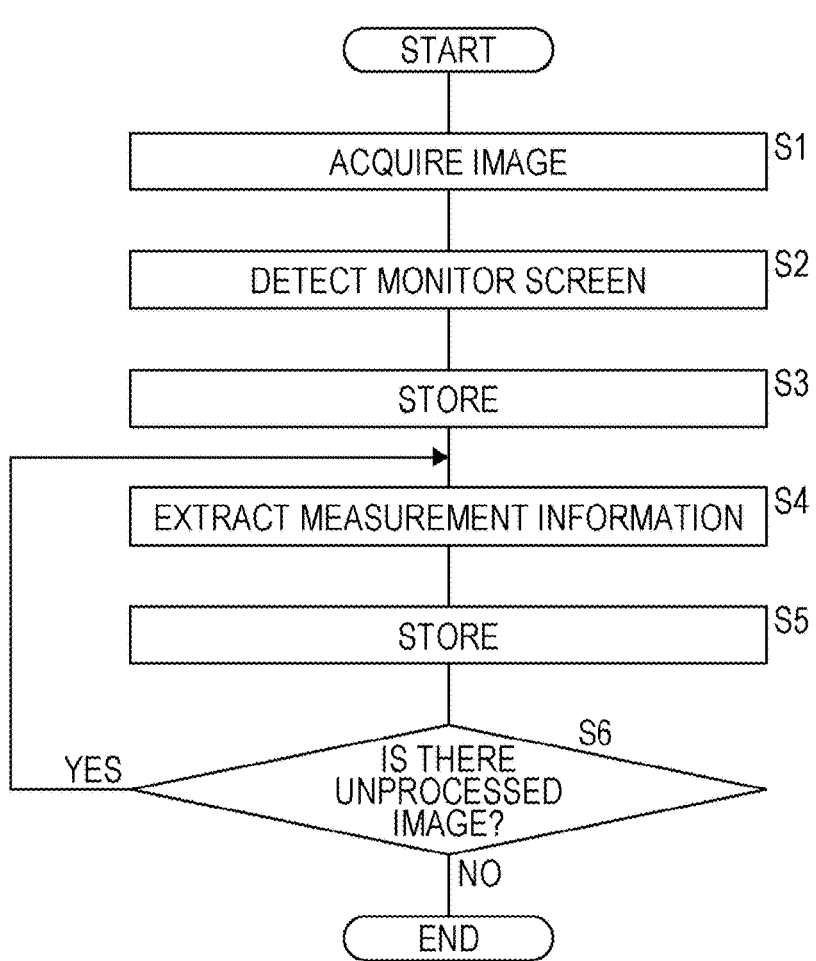
FIG. 4 is an explanatory diagram illustrating one example of a record layout in a measurement information DB.
FIG. 5 is a flowchart illustrating a procedure of information processing performed by a control unit of the information processing device according to the first embodiment.

The control unit 51 uses the detection result of the monitor screen to extract information regarding the monitor screen from the image in the region coordinates. The information regarding the monitor screen includes various types of measurement information displayed on the monitor screen, and may be a measurement value, text data, graph data, or a medical image such as an intravascular ultrasound (IVUS) image or an angiographic image. In the present embodiment, the measurement information will be described using a measurement value as an example. Regarding the processing of extracting the measurement value, the control unit 51 recognizes the number on the monitor screen included in the surgical space image using, for example, a learning model that is trained by machine learning in advance. The learning model is trained by machine learning in advance so as to receive, for example, data of a monitor image including data of a surgical space image and region coordinates of a monitor screen as an input, and output, for each of the numbers on the monitor screen included in this image, the probabilities of the number being "0" to "9". Note that the region coordinates of the monitor screen used in the processing of extracting the measurement value are not limited to the coordinates output by the learning model described above, and may be coordinates input by the operational personnel using the operation unit 57 while observing the surgical space image. Alternatively, data of the image region of the monitor screen extracted from the surgical space image may be used as an input to the learning model. The learning model is trained by machine learning using, for example, training data in which the data of the monitor image is associated with a label indicating the probability of each number in the image within the region coordinates being "0" to "9". In the first embodiment, the control unit 51 inputs the data of the monitor image to the learning model, and acquires the probabilities of each number output from the learning model being "0" to "9". By specifying a number corresponding to a probability higher than a predetermined threshold (for example, 80%) from the probabilities, a measurement value on the monitor screen is extracted. The data of the measurement value extracted by the control unit 51 is stored in the measurement information DB 542 of the mass storage unit 54. As a result, the accuracy of the measurement value can be improved. FIG. 4 is an explanatory diagram illustrating one example of a record layout in the measurement information DB 542. As illustrated in FIG. 4, the measurement information DB 542 includes an imaging date-and-time column and a measurement information column. The imaging date-and-time column stores imaging dates and times of images. The measurement information column stores the recognized measurement values for each of the monitors 201, 211, 221, . . . . Note that the measurement information DB 542 may include other columns such as a monitor screen column and an abnormality type column as described later.

Furthermore, when the probabilities of a certain number output from the learning model being "0" to "9" output from the learning model are all equal to or less than a predetermined threshold (for example, 50%), the control unit 51 determines that the identification rate for the number is low and does not store the measurement value indicated by the number in the measurement information DB 542. Note that the control unit 51 may create a trend graph using the measurement information stored in the measurement information DB 542 and display the trend graph on the display unit 56.

FIG. 5 is a flowchart illustrating a procedure of information processing performed by the control unit 51 of the information processing device 50 according to the first embodiment.

The control unit 51 acquires the surgical space image captured by the imaging device 10 (step S1), detects the monitor screen from the acquired image (step S2), and stores data of the detected monitor image in the image DB 541 (step S3).

The control unit 51 extracts information regarding the monitor screen from the data of the monitor image stored in the image DB 541 (step S4), and stores the extracted information in the measurement information DB 542 together with the imaging date and time (step S5).

The control unit 51 determines whether or not there is an unprocessed monitor image, and when determining that there is an unprocessed monitor image (YES in step S6), returns the processing to step S4. When determining that there is no unprocessed monitor image (NO in step S6), the control unit 51 ends the processing.

In the first embodiment, the surgical space in the operating room 100 is imaged, and the information regarding the monitor screen is extracted from the surgical space image and stored, whereby the measurement information about each of the measurement devices 20, 21, 22, . . . in the imaging region can be automatically recorded. Since the information about the plurality of medical devices is collectively managed, it is possible to reduce the burden on a medical profession and avoid human errors due to manual recording. In addition, it is not necessary to provide wires between each of the measurement devices 20, 21, 22, . . . and the information processing device 50, whereby it is possible to eliminate the trouble of routing the wires for the medical devices and to reduce various risks (for example, erroneous recognition due to cable noise, entanglement between cables, the cables getting in the way when the measuring device is moved in the operating room or when the operator himself/herself moves, or the like) caused by very complicated wiring in a medical environment. Furthermore, when a medical device is newly introduced, large-scale software revision is not required even if the communication protocol is not prepared.

In addition, it is possible to, for example, illustrate time-series data of a mode of a patient graphically (for example, with a trend graph) using the recorded measurement information. The recorded measurement information has no outlier caused by cable noise or human error, and thus, highly accurate trend information can be obtained when a trend graph is created using the extracted measurement information. In addition, when the identified measurement information is not reliable, the measurement information is not recorded. Therefore, an accurate trend graph can be created without using an identification result with low reliability.

Note that the surgical space image may include a blood tank of the extracorporeal circulation device and each circuit in addition to the monitor screen. The information processing system according to the first embodiment can easily monitor the liquid level of the extracorporeal circulation device by extracting information related to the liquid level of the blood tank from the surgical space image.

Second Embodiment

An information processing system according to the second embodiment is different from the first embodiment in including a plurality of imaging devices, and thus, the above difference will be mainly described below. The other configurations, operation, and effect are similar to those of the first embodiment, and thus, the corresponding portions are denoted by the same reference numerals, and the detailed description thereof will be omitted.

Figures 6, 7:
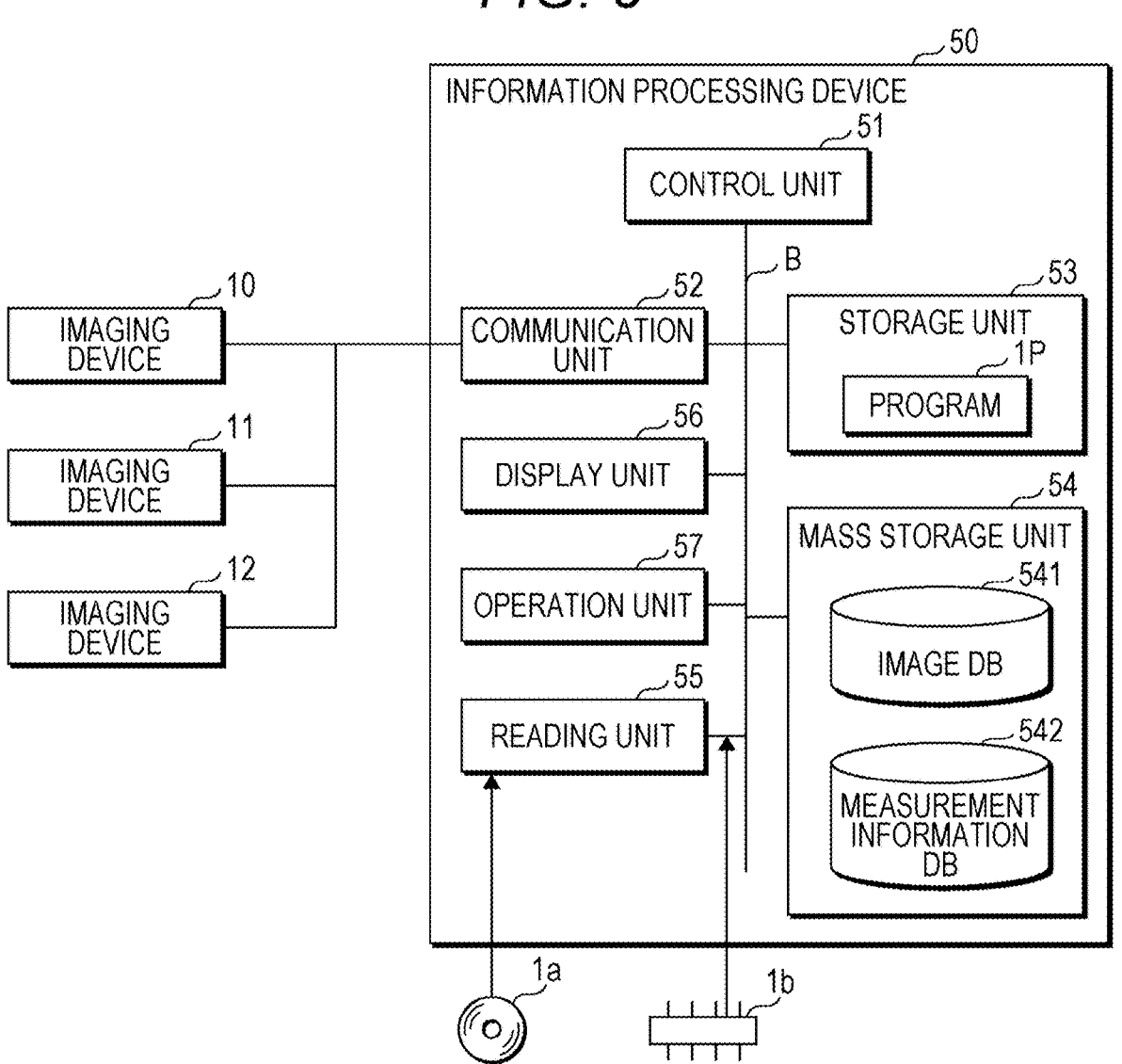
FIG. 6 is a block diagram illustrating an example of the configuration of an information processing system according to a second embodiment.
FIG. 7 is an explanatory diagram illustrating one example of selection processing performed by a control unit of an information processing device according to the second embodiment.

FIG. 6 is a block diagram illustrating an example of the configuration of the information processing system according to the second embodiment. Imaging devices 10, 11, 12, . . . are installed at different locations in an operating room 100, capture an image of a surgical space in the operating room 100 at different angles to obtain a plurality of surgical space images, and transmit the obtained images to an information processing device 50. Although FIG. 6 illustrates three imaging devices, the number of imaging devices is not limited to three, and may be two, four, or more than four.

In the information processing device 50, a control unit 51 acquires a plurality of surgical space images via a communication unit 52, selects one image from the plurality of surgical space images according to the installation location of each of the imaging devices 10, 11, 12, . . . , and extracts information regarding a monitor screen from the selected image.

A storage unit 53 stores, for each of monitors 201, 211, 221, . . . , a priority table (not illustrated) in which priorities of the imaging devices 10, 11, 12, . . . are set in advance on the basis of the installation locations of the imaging devices. When detecting the monitor screen, the control unit 51 uses, for the monitor to be detected, the surgical space image captured by the imaging device having the highest priority on the basis of the priority table. Note that the method for setting the priority is not limited to the above method, and the priority may be set for each surgical space image by comparing the accuracy among surgical space images captured by the imaging devices 10, 11, 12, . . . at the same time point.

In a case where it is impossible to detect the monitor screen or recognize the measurement information because a blocking object is included in the surgical space image captured by the imaging device having the highest priority, the control unit 51 performs the processing of detecting the monitor screen again using the surgical space image captured by the imaging device with the second highest priority. The control unit 51 recognizes a blocking object by, for example, a technology called "YOLO" that detects an object such as a person from an image using a learning model trained by deep learning. FIG. 7 is an explanatory diagram illustrating one example of selection processing performed by the control unit 51 of the information processing device 50 according to the second embodiment. FIG. 7 illustrates a recognition status of the monitor 201 based on the surgical space images respectively captured by the imaging devices 10, 11, and 12 at each time point. In FIG. 7, a circle indicates that it is possible to recognize, and a cross indicates that it is impossible to recognize. As illustrated in FIG. 7, the measurement information displayed on the monitor 201 cannot be recognized from the surgical space image captured by the imaging device 10 at the time point T2. The control unit 51 selects the surgical space image captured by the imaging device 11 and performs the processing of detecting the monitor screen again.

Figure 8:
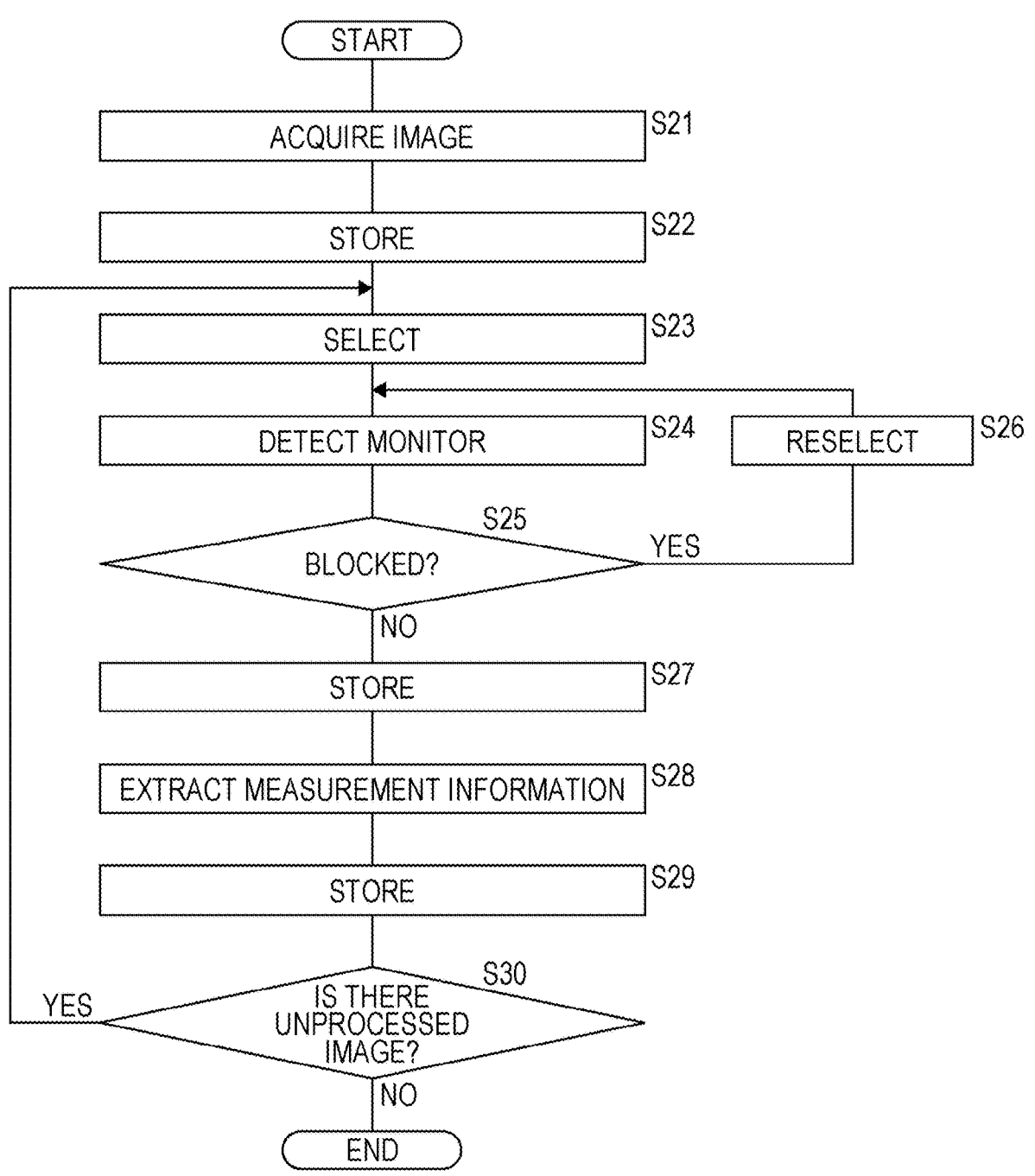
FIG. 8 is a flowchart illustrating a procedure of information processing performed by the control unit of the information processing device according to the second embodiment.

FIG. 8 is a flowchart illustrating a procedure of information processing performed by the control unit 51 of the information processing device 50 according to the second embodiment.

The control unit 51 acquires a plurality of surgical space images captured by the imaging devices 10, 11, 12, . . . (step S21), and stores the acquired images in an image DB 541 of a mass storage unit 54 (step S22).

The control unit 51 selects one image from the plurality of surgical space images on the basis of the priority table (step S23), and detects the monitor screen from the selected surgical space image (step S24). The control unit 51 determines whether or not the monitor screen is blocked by the blocking object (step S25). When determining that the monitor screen is blocked (YES in step S25), the control unit 51 selects another image from the plurality of surgical space images on the basis of the priority table (step S26), and returns the processing to step S24.

When determining that the monitor image is not blocked (NO in step S25), the control unit 51 stores data of the detected monitor image in the image DB 541 (step S27).

The control unit 51 extracts information regarding the monitor screen on the basis of the data of the monitor image stored in the image DB 541 (step S28), and stores the extracted information in the measurement information DB 542 of the mass storage unit 54 together with the imaging date and time (step S29).

The control unit 51 determines whether or not there is an unprocessed monitor image (step S30), and when determining that there is an unprocessed monitor imaged (YES in step S30), returns the processing to step S23. When determining that there is no unprocessed monitor image (NO in step S30), the control unit 51 ends the processing.

In the second embodiment, the plurality of imaging devices 10, 11, 12, . . . is installed. Therefore, when the measurement information is not recognized from one surgical space image, another surgical space image can be used to complement the measurement information. Therefore, the information about the medical device can be accurately recorded. In addition, by using the surgical space image captured by the imaging device with high reliability for each monitor screen, information about the medical device can be recorded with higher accuracy.

Third Embodiment

An information processing system according to the third embodiment is different from the first embodiment in that an information processing device 50 recognizes a blocking object present between each of monitor screens and an imaging device 10, and thus, the above difference will be mainly described below. The other configurations, operation, and effect are similar to those of the first embodiment, and thus, the corresponding portions are denoted by the same reference numerals, and the detailed description thereof will be omitted.

A control unit 51 recognizes a blocking object present between the monitor screen and the imaging device 10, and extracts information regarding the monitor screen except for a region of the recognized blocking object. In addition, when recognizing an operator as the blocking object, the control unit 51 specifies the position of the recognized operator.

The control unit 51 recognizes a blocking object by, for example, a technology called "YOLO" that detects an object such as a person from an image using a learning model trained by deep learning. For example, in a case where the display screen of the monitor 201 is blocked by the operator in the surgical space image captured by the imaging device 10 at a certain time point, the control unit 51 specifies the position of the operator as a point on a straight line between the imaging device 10 and the monitor 201. Note that, even in a case where a part of the display screen of the monitor 201 is blocked by the operator, information may be extracted from a region that is not blocked. In this case, the control unit 51 specifies a pixel region of the operator on the display screen using a machine learning model of a segmentation method such as SegNet. The control unit 51 extracts an image in a pixel region other than the specified pixel region on the display screen. The control unit 51 recognizes measurement information in the region by a machine learning model or pattern matching that performs character recognition.

Figure 9:
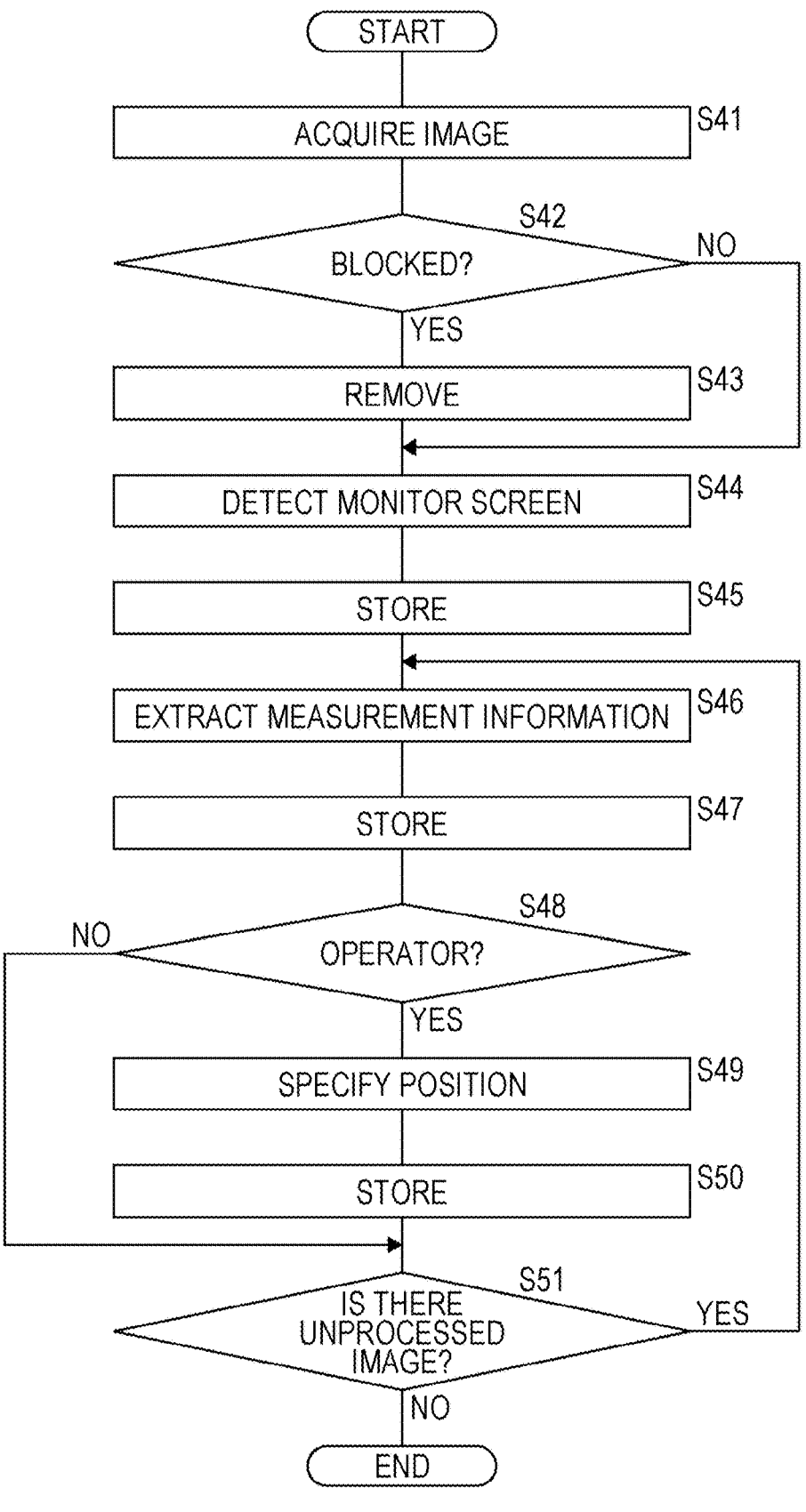
FIG. 9 is a flowchart illustrating a procedure of information processing performed by a control unit of an information processing device according to a third embodiment.

FIG. 9 is a flowchart illustrating a procedure of information processing performed by the control unit 51 of the information processing device 50 according to the third embodiment.

In the information processing device 50, the control unit 51 acquires the surgical space image captured by the imaging device 10 (step S41), and determines whether or not the monitor screen in the acquired surgical space image is blocked (step S42). When determining that the monitor screen is blocked (YES in step S42), the control unit 51 removes the blocked screen region (step S43), detects the monitor screen for the region that is not blocked (step S44), and stores data of the detected monitor image in the image DB 541 (step S45).

The control unit 51 extracts information regarding the monitor screen from the data of the monitor image stored in the image DB 541 (step S46), and stores the extracted information in the measurement information DB 542 together with the imaging date and time (step S47).

The control unit 51 determines whether or not the blocking object is an operator (step S48). When determining that the blocking object is the operator (YES in step S48), the control unit 51 specifies the position of the operator as a position between the monitor 201 and the imaging device 10, between the monitor 211 and the imaging device 10, or between the monitor 221 and the imaging device 10 (step S49), and stores the specified position in the measurement information DB 542 together with the imaging date and time (step S50). The control unit 51 determines whether or not there is an unprocessed monitor image (step S51), and when determining that there is an unprocessed monitor imaged (YES in step S51), returns the processing to step S46. When determining that there is no unprocessed monitor image (NO in step S51), the control unit 51 ends the processing.

When determining that the blocking object is not the operator (NO in step S48), the control unit 51 returns the processing to step S51.

In the third embodiment, the measurement information can be extracted from the monitor screen not blocked by the blocking object, and the position of the operator can be specified and recorded.

Fourth Embodiment

An information processing system according to the fourth embodiment is different from the first embodiment in that an information processing device 50 further acquires an actual measurement value by each measurement device, and thus, the above difference will be mainly described below. The other configurations, operation, and effect are similar to those of the first embodiment, and thus, the corresponding portions are denoted by the same reference numerals, and the detailed description thereof will be omitted.

Figure 10:
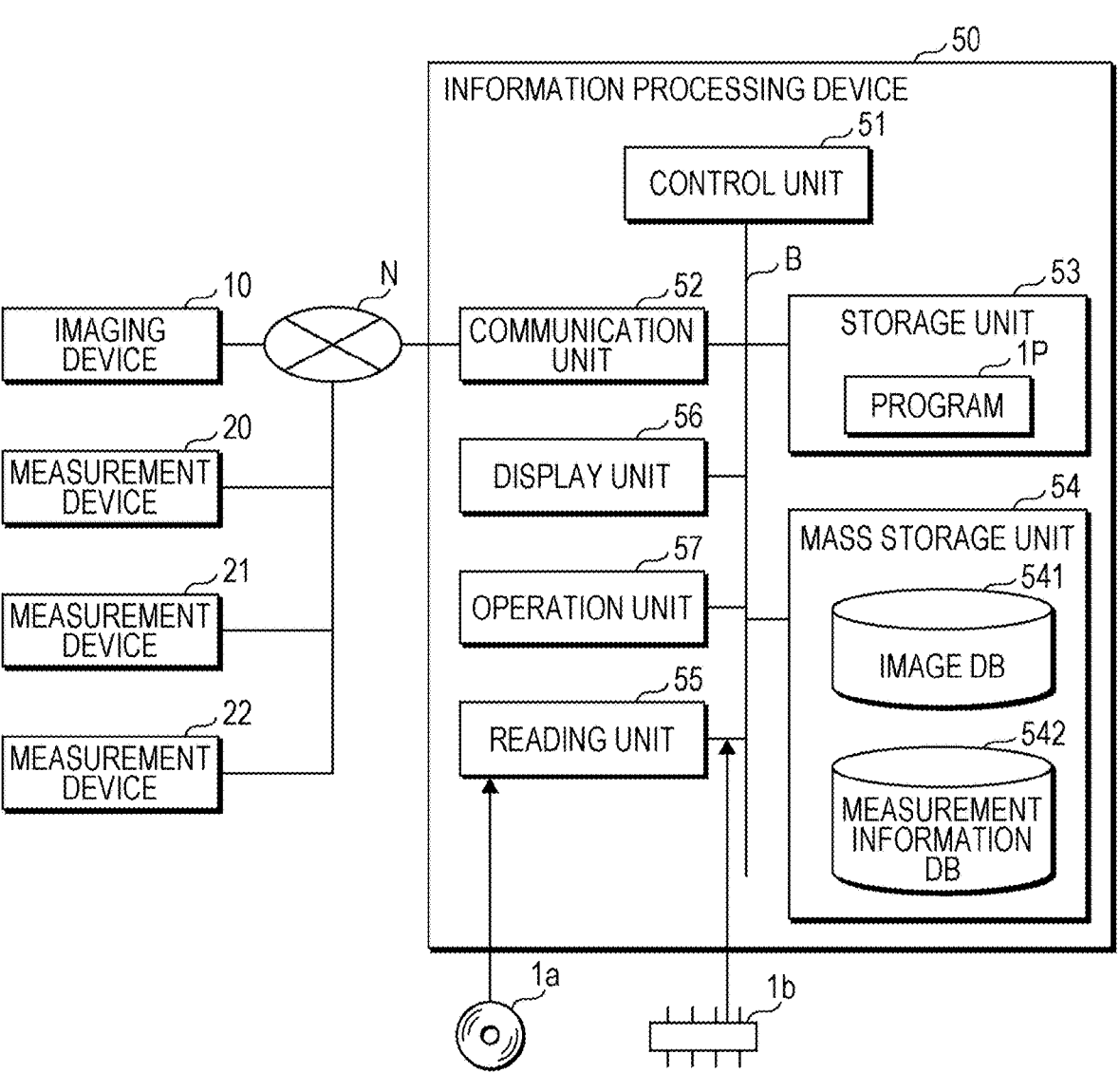
FIG. 10 is a block diagram illustrating an example of the configuration of an information processing system according to a fourth embodiment.

FIG. 10 is a block diagram illustrating an example of the configuration of the information processing system according to the fourth embodiment. A plurality of measurement devices 20, 21, 22, . . . transmits measured actual measurement values to the information processing device 50 via a network N. The measurement devices 20, 21, 22, . . . and the information processing device 50 are connected via the network N, but may be directly connected by a wired cable, or wirelessly connected using, for example, Bluetooth (registered trademark) to exchange information.

In the information processing device 50, a control unit 51 compares the actual measurement values measured by the measurement devices 20, 21, 22, . . . with a measurement value (hereinafter, referred to as extracted measurement value) extracted from the surgical space image, and in a case where a difference between them is equal to or greater than a predetermined threshold, stores the monitor screen from which the measurement value is extracted and the imaging date and time in a measurement information DB 542 of a mass storage unit 54 in association with each other. Here, the predetermined threshold may be appropriately set as necessary and stored in a storage unit 53 in advance. Note that, in a case where the information regarding the monitor screen extracted from the surgical space image is graph data, the control unit 51 may convert the graph data into a plurality of extracted measurement values and compare the converted extracted measurement values with the actual measurement values.

FIG. 11 is a flowchart illustrating a procedure of information processing performed by the control unit 51 of the information processing device 50 according to the fourth embodiment.

The control unit 51 acquires an actual measurement value (step S61), and compares the acquired actual measurement value with an extracted measurement value which is stored in the measurement information DB 542 and which corresponds to the imaging date and time which is the same as the acquisition date and time (step S62).

The control unit 51 determines whether or not the difference between them is equal to or greater than a predetermined threshold (step S63). When determining that the difference is equal to or greater than the predetermined threshold (YES in step S63), the control unit 51 stores the monitor screen displaying the extracted measurement value in the measurement information DB 542 in association with the imaging date and time (step S64).

The control unit 51 outputs warning information to the display unit 56 (step S65) indicating that the difference is equal to or greater than a predetermined threshold, and ends the processing.

When determining that the difference is not equal to or greater than the predetermined threshold (NO in step S63), the control unit 51 ends the processing.

FIGS. 12 and 13 are schematic diagrams illustrating an example of warning information to be displayed on the display unit 56. The control unit 51 creates trend graphs on the basis of the extracted measurement values and the actual measurement values, and displays the trend graphs on the display unit 56. In FIGS. 12 and 13, the horizontal axis indicates time point, the vertical axis indicates measurement value, black triangles indicate actual measurement values, and black circles indicate extracted measurement values. At time point 6, the difference between the actual measurement value and the extracted measurement value is equal to or greater than the predetermined threshold, and thus, an arrow indicating the difference between the actual measurement value and the extracted measurement value is displayed on the trend graphs as illustrated in FIG. 12. In the trend graphs created thereafter, the actual measurement value and the extracted measurement value at time point 6 are emphasized by circles as illustrated in FIG. 13.

In the fourth embodiment, it is possible to determine whether or not an abnormality occurs in the measurement device by comparing the actual measurement value with the extracted measurement value. In a case where there is an abnormality in the measurement device, warning information is displayed, by which the status of the abnormality can be clearly provided. Furthermore, it is also possible to omit in advance the extracted measurement value determined to be an abnormal value, and this has not been conceived of in the related art.

Fifth Embodiment

An information processing system according to the fifth embodiment is different from the first embodiment in that an information processing device 50 detects the abnormality of a patient (subject), and thus, the above difference will be mainly described below. The other configurations, operation, and effect are similar to those of the first embodiment, and thus, the corresponding portions are denoted by the same reference numerals, and the detailed description thereof will be omitted.

In the information processing device 50, a control unit 51 detects an abnormality of the patient on the basis of various types of measurement information stored in a measurement information DB 542. For example, a storage unit 53 may store in advance a table in which a numerical value indicating a normal range is set for each measurement item, and it may be determined that an abnormality occurs when the measurement information about the patient is outside the normal range with reference to the table. Alternatively, the storage unit 53 may store in advance a table in which information indicating a normal trend is set for each measurement item, and it may be determined that an abnormality occurs when the trend of the measurement information about the patient is different from the normal trend with reference to the table.

When determining that there is an abnormality, the control unit 51 outputs information regarding the abnormality to the display unit 56. The information regarding the abnormality may be information presenting an abnormal measurement value or trend information, or may be information presenting a measurement item in which an abnormality has occurred. When determining that there is an abnormality, the control unit 51 may output advice information for eliminating the abnormality to the display unit 56.

The present embodiment will describe a case where the measurement device is an extracorporeal circulation device as an example. FIG. 14 is a reference table for abnormality determination of the extracorporeal circulation device. The table records trend information about trends of various measurement values by the extracorporeal circulation device, a type of abnormality, and advice information upon the occurrence of abnormality in association with each other. The reference table is stored in advance in the storage unit 53, for example. As illustrated in FIG. 14, the reference table includes an abnormality type column, a measurement item column, and an advice column. In the abnormality type column, abnormality A, abnormality B, abnormality C, and abnormality D are recorded as the types of abnormality. In the measurement item column, a change in flow rate or pressure per unit time is recorded for each of measurement items K1, K2, K3, and K4. In the advice column, advice for each type of abnormality is recorded. In the reference table illustrated in FIG. 14, the intensity of change of each measurement item is represented by x, 2x, and 3x in the order of "low", "medium", and "high", and the direction of change is represented by "+" indicating an increasing trend and "−" indicating a decreasing trend. Here, the level of the intensity of change may be appropriately set in advance as necessary.

Specifically, the control unit 51 calculates a change in the flow rate or the pressure per unit time for each measurement item, stores the calculated change in, for example, the mass storage unit 54, determines whether or not an abnormality has occurred on the basis of the reference table, specifies the type of the abnormality when determining that the abnormality has occurred, and outputs advice information for eliminating the abnormality to the display unit 56. For example, when each of the measurement items K1, K2, K3, and K4 shows a decreasing trend, the control unit 51 determines that there is abnormality A, and displays (outputs) a message indicating "there may be a thrombus in the cannula for drawing blood" on the display unit 56 as advice information for eliminating the abnormality. In addition, the control unit 51 may display the type of abnormality on the display unit 56 together with the advice information. Furthermore, the control unit 51 may display, on the display unit 56, a combination of the trend information about various measurement values by the extracorporeal circulation device and the advice information. Alternatively, the control unit 51 may display an image according to the reference table on the display unit 56.

Note that the control unit 51 may determine the possibility of abnormality in the patient when detecting that the abnormality information is displayed on the monitor screen. When determining that there is an abnormality, the control unit 51 may store the monitor screen on which the abnormality information is displayed in the measurement information DB 542 in association with the imaging date and time.

Figure 15:
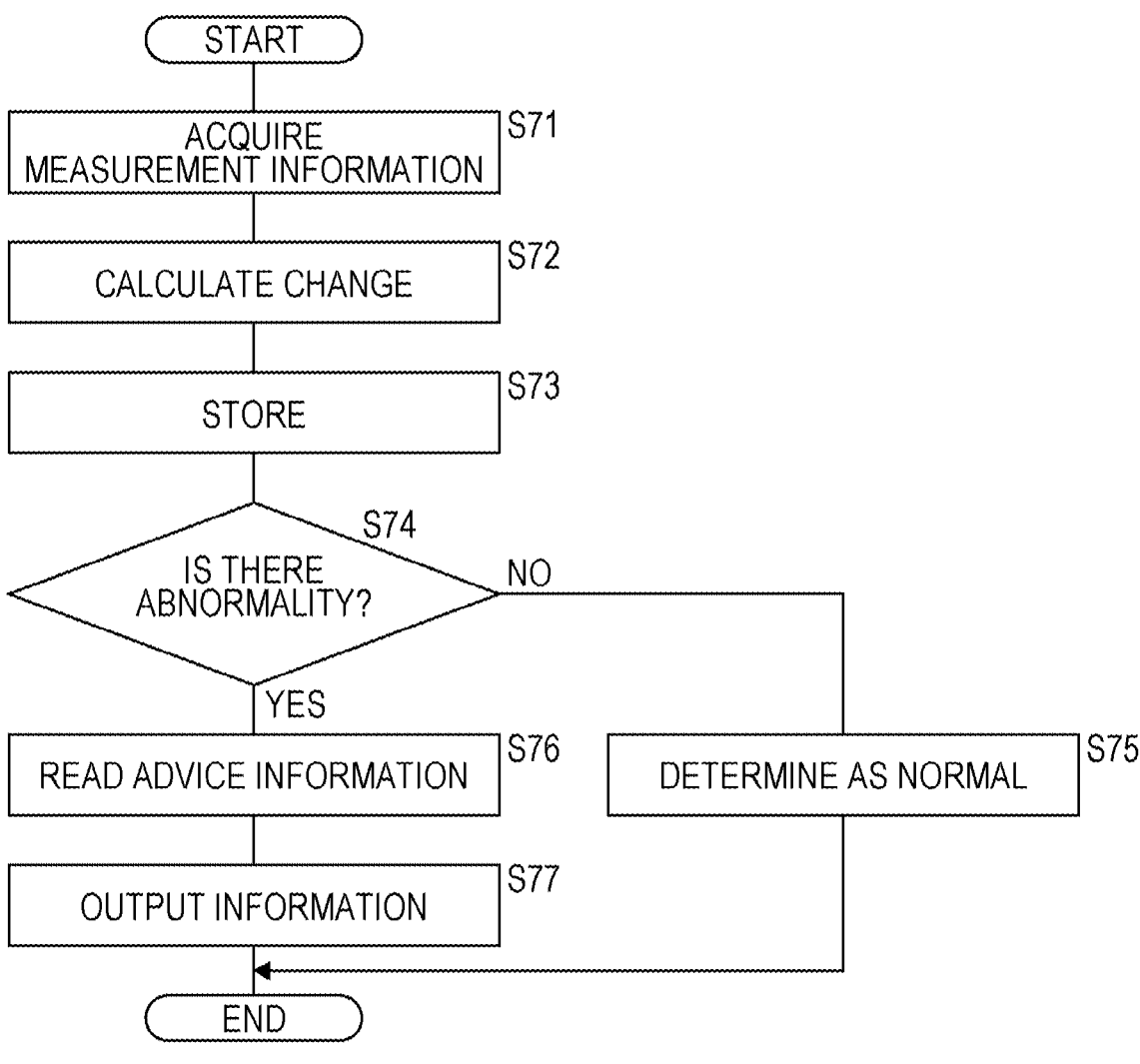
FIG. 15 is a flowchart illustrating a procedure of information processing performed by a control unit of an information processing device according to a fifth embodiment.

FIG. 15 is a flowchart illustrating a procedure of information processing performed by the control unit 51 of the information processing device 50 according to the fifth embodiment.

The control unit 51 acquires measurement information for each measurement item (step S71), calculates a change in the measurement information about each measurement item (step S72), and stores the calculated change in the measurement information in the mass storage unit 54 (step S73). The control unit 51 determines whether or not there is an abnormality in the measurement information on the basis of the reference table (step S74), and when determining that there is no abnormality (NO in step S74), the control unit 51 determines that the measurement information is normal (step S75), and ends the processing.

When determining that there is an abnormality (YES in step S74), the control unit 51 reads advice information for eliminating the abnormality from the reference table (step S76), outputs the read advice information to the display unit 56 (step S77), and ends the processing.

In the fifth embodiment, when there is an abnormality in information about a medical device, the content of the abnormality can be recorded, and a countermeasure can be presented depending on the abnormality. Therefore, the burden on a medical profession can be reduced.

Sixth Embodiment

An information processing system according to the sixth embodiment is different from the first embodiment in that an information processing device 50 further performs behavior recognition processing on the basis of an image of an operator included in a surgical space image, and thus, the above difference will be mainly described below. The other configurations, operation, and effect are similar to those of the first embodiment, and thus, the corresponding portions are denoted by the same reference numerals, and the detailed description thereof will be omitted.

Figure 16:
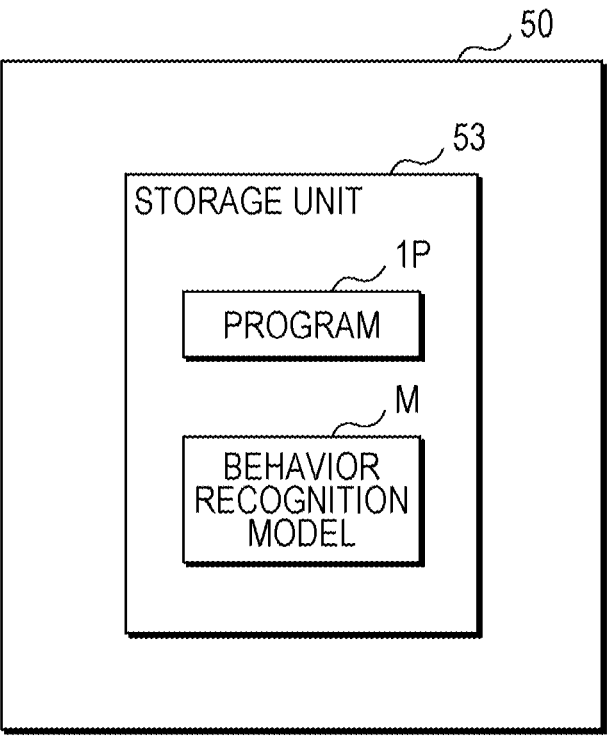
FIG. 16 is a block diagram illustrating a configuration example of a storage unit of an information processing device according to a sixth embodiment.

FIG. 16 is a block diagram illustrating a configuration example of a storage unit 53 of the information processing device 50 according to the sixth embodiment. The storage unit 53 of the information processing device 50 further stores a behavior recognition model M that is a trained model trained by machine learning. The behavior recognition model M is assumed to be used as a program module functioning as a part of artificial intelligence software.

An imaging device 10 captures an image of a surgical space and sequentially acquires the surgical space image of one frame. The imaging device 10 is configured to acquire surgical space images of 60 frames, 30 frames, or 15 frames per second, for example, and the surgical space images acquired by the imaging device 10 are sequentially transmitted to the information processing device 50.

In addition to extracting the information regarding the monitor screen, the control unit 51 performs behavior recognition processing of recognizing the behavior of an operator in the surgical space imaged by the imaging device 10, and stores information regarding the recognized behavior of the operator and the information regarding the monitor screen in time series in association with each other. With respect to the behavior recognition processing, the control unit recognizes the behavior of the operator from the surgical space image using the behavior recognition model M stored in the storage unit 53. The behavior of the operator includes, but is not limited to, incision, suture, injection, endoscopic operation, catheter insertion, balloon expansion, use of an electric scalpel, hemostasis, waiting, and the like.

Figure 17:
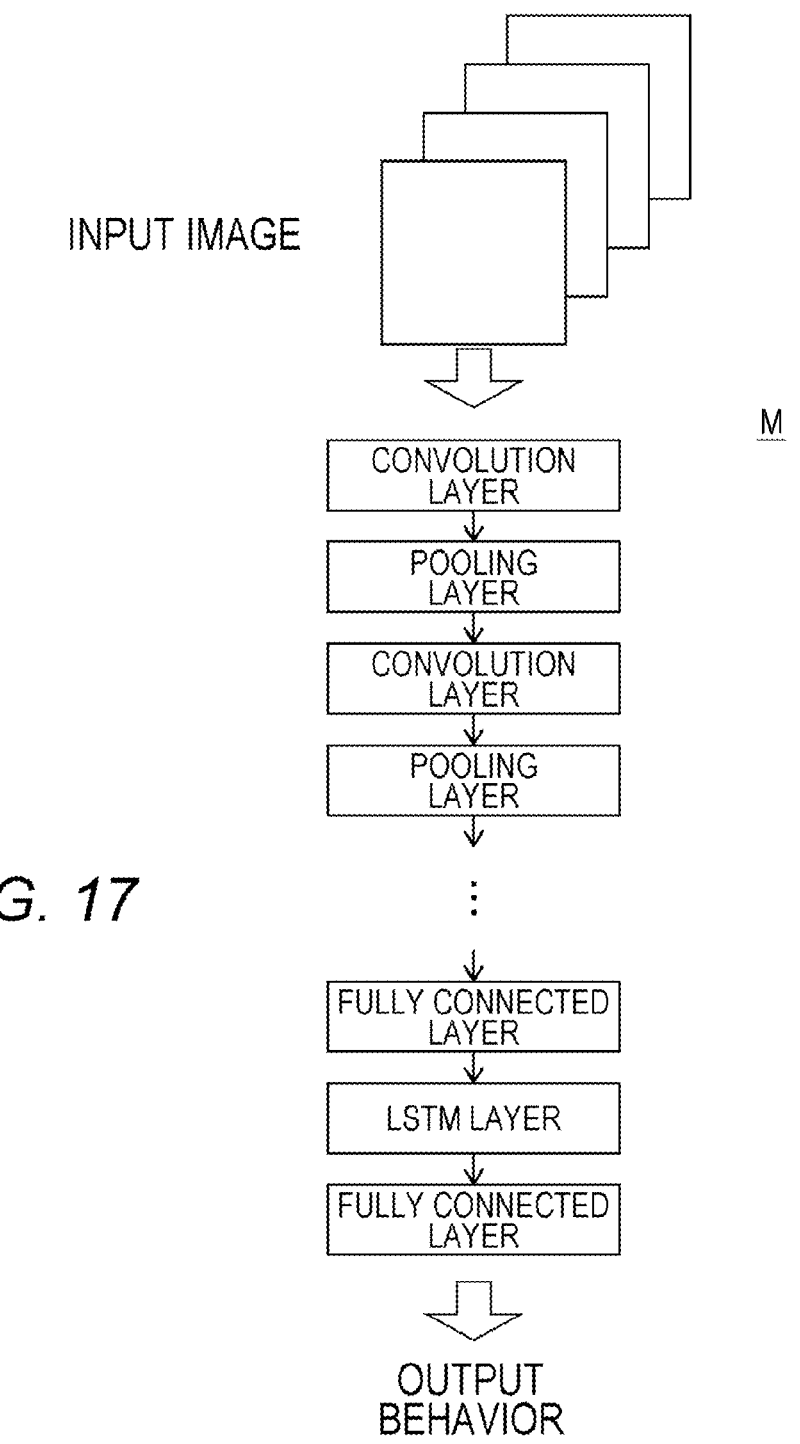
FIG. 17 is a schematic diagram illustrating a configuration example of a behavior recognition model.

FIG. 17 is a schematic diagram illustrating a configuration example of the behavior recognition model M. The behavior recognition model M in the present embodiment is configured by combining an object detection algorithm (neural network) and a long short-term memory (LSTM) as illustrated in FIG. 17, for example. As the object detection algorithm, regions with convolution neural network (R-CNN), Fast R-CNN, Faster R-CNN, Mask R-CNN, single shot multibook detector (SSD), you only look once (YOLO), or the like can be used. The behavior recognition model M is a trained model trained to receive, as an input, a time-series surgical space image including the operator, calculate whether or not the imaged operator is performing a predetermined behavior on the basis of the input image, and output a calculation result.

The behavior recognition model M illustrated in FIG. 17 includes a convolution layer, a pooling layer, an LSTM layer, and a fully connected layer. In the behavior recognition model M in the present embodiment, a plurality of frames of surgical space images over a predetermined unit time is input via an input layer. From the surgical space image of each frame input via the input layer, a feature amount of the image is extracted by filter processing or the like in the convolution layer to generate a feature map, and the position sensitivity of the feature amount of the image is lowered in the pooling layer, by which it is possible to recognize even when the position of the feature amount deviates from the position of the feature map. A plurality of the convolution layers and a plurality of the pooling layers are repeatedly provided, and the feature map generated by the plurality of convolution layers and the pooling layers is input to the fully connected layer, then input to the LSTM layer, and further input to the fully connected layer. Each of the fully connected layer and the LSTM layer calculates an output value of a node of each layer using various functions, thresholds, and the like on the basis of the input feature map, and sequentially inputs the calculated output value of the node of each layer to a node of a subsequent layer, and the fully connected layer in the last stage gives the output values to output nodes of the output layer, respectively. In the behavior recognition model M, the number of input nodes of the input layer, the number of the convolution layers, the number of the pooling layers, and the number of the fully connected layers are not limited to those illustrated in FIG. 17. Note that an image obtained by extracting a skeleton by VisionPose (from NEXT-SYSTEM Company, Ltd.) or the like may be input as the input image.

The behavior recognition model M learns using training data including a correct answer label indicating each behavior and a captured image obtained by imaging a person performing the behavior. When the captured image included in the training data is input, the behavior recognition model M learns so as to output a discrimination label corresponding to the behavior indicated by the correct answer label included in the training data. In the learning processing, the behavior recognition model M learns so as to optimize a weighting coefficient that couples the nodes of each layer and the coefficient of a function. Thus, the trained behavior recognition model M is obtained that is trained to, when receiving the captured image as an input, specify the behavior performed by the person included in the captured image and output information regarding the behavior as a result of specifying the behavior. Note that, as the captured image used for the training data, images obtained by capturing persons performing various different behaviors can be used as images of the respective behaviors.

The behavior recognition model M in the present embodiment may receive, for example, captured images of a plurality of frames sequentially captured by the imaging device 10, or captured images of a plurality of frames extracted at predetermined time intervals (for example, 1 second) from the captured images captured by the imaging device 10. The behavior recognition model M is trained by another learning device, but may be trained by the information processing device 50. The behavior recognition model M is not limited to the neural network as illustrated in FIG. 17, and learning models constructed by various machine learning algorithms can be used.

The control unit 51 stores the information regarding the behavior of the operator output from the behavior recognition model M in a measurement information DB 542. In addition, when determining that an abnormality occurs as a result of determining whether or not an abnormality occurs and specifying the type of the abnormality as in the above-described fourth and fifth embodiments, the control unit 51 outputs abnormality information including the behavior of the operator and the type of the abnormality to the display unit 56.

FIG. 18 is an explanatory diagram illustrating another example of a record layout in the measurement information DB 542. The measurement information DB 542 includes an imaging date-and-time column, a measurement information column, an abnormality flag column, an operator behavior column, and an abnormality type column. The imaging date-and-time column stores information about the imaging date and time of an image. The measurement information column stores the extracted measurement information. The abnormality flag column stores a flag indicating whether or not an abnormality occurs. When it is determined that there is an abnormality, such as when it is determined that the actual measurement value and the extracted measurement value do not match as in the fourth embodiment, or when it is determined that the measurement information is not normal as in the fifth embodiment, "1" is stored, and when it is determined that there is no abnormality, "0" is stored. The operator behavior column stores the information regarding the behavior of the operator output from the behavior recognition model M. The abnormality type column stores information regarding an abnormality type. For example, "none" is stored when it is determined that there is no abnormality, and the type of abnormality is stored when the type of abnormality can be identified as in the fifth embodiment. In addition, in a case where it is determined that there is no abnormality in the fifth embodiment, but the abnormality flag is 1, and the operator uses a surgical tool that is likely to generate noise, such as an electric scalpel, the type of abnormality is indicated as "noise". Note that the measurement information DB 542 may further store a surgical space image, a monitor image, and the like.

FIG. 19 is a flowchart illustrating a procedure of information processing performed by the control unit 51 of the information processing device 50 according to the sixth embodiment.

The control unit 51 acquires the surgical space image (step S81) and inputs the image to the behavior recognition model M (step S82). The control unit 51 acquires the information regarding the behavior of the operator output from the behavior recognition model M (step S83), and stores the acquired information in the measurement information DB 542 in association with the measurement information (step S84).

The control unit 51 determines whether or not the abnormality flag is set (step S85), and when determining that the abnormality flag is not set (NO in step S85), the control unit 51 stores the type of the abnormality as "none" (step S86), and ends the processing.

When determining that the abnormality flag is set (YES in step S85), the control unit 51 determines whether or not the type of the abnormality has been identified (step S87). When determining that the type of the abnormality has been identified (YES in step S87), the control unit 51 stores the identified type of the abnormality in the abnormality type column of the measurement information DB 542 (step S88), outputs the abnormality information to the display unit 56 (step S89), and ends the processing.

When determining that the type of the abnormality has not been identified (NO in step S87), the control unit 51 determines whether or not the behavior of the operator corresponds to a behavior that is likely to generate noise (step S90). When determining that the behavior of the operator corresponds to the behavior that is likely to generate noise (YES in step S90), the control unit 51 stores "noise" as the type of the abnormality in the abnormality type column of the measurement information DB 542 (step S91), and returns the processing to step S89.

When determining that the behavior of the operator does not correspond to the behavior which is likely to generate noise (NO in step S90), the control unit 51 stores "unknown" as the type of abnormality in the abnormality type column of the measurement information DB 542 (step S92), outputs a message indicating "Please check the device" to the display unit 56 (step S93), and ends the processing.

In the sixth embodiment, it is possible to support determination of the cause of the abnormality in the measurement information by specifying the type of the behavior of the operator and recording the type together with the measurement information.

Seventh Embodiment

An information processing system according to the seventh embodiment is different from the first embodiment in that an information processing device 50 does not store the detection result of the monitor screen, and thus, the above difference will be mainly described below. The other configurations, operation, and effect are similar to those of the first embodiment, and thus, the corresponding portions are denoted by the same reference numerals, and the detailed description thereof will be omitted.

Figure 20:
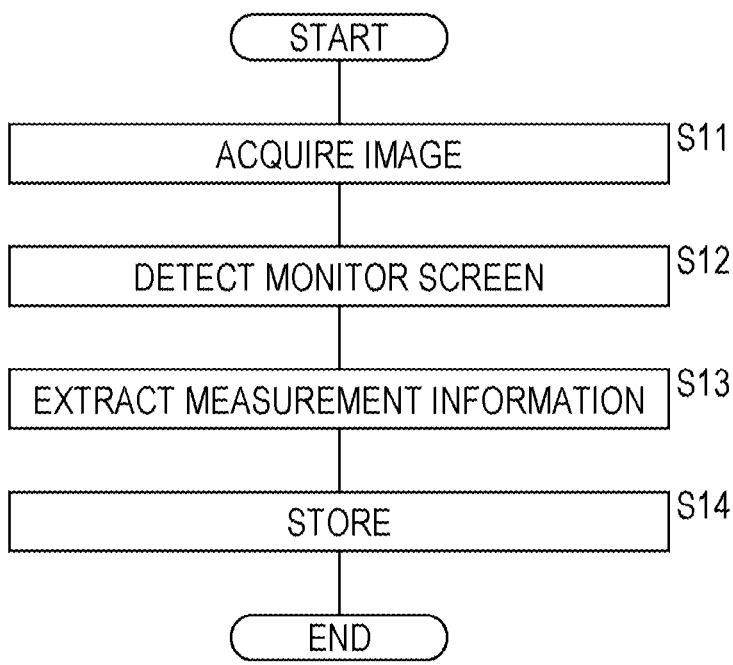
FIG. 20 is a flowchart illustrating a procedure of information processing performed by a control unit of an information processing device according to a seventh embodiment.

FIG. 20 is a flowchart illustrating a procedure of information processing performed by a control unit 51 of the information processing device 50 according to the seventh embodiment.

The control unit 51 acquires a surgical space image captured by an imaging device 10 (step S11), and detects a monitor screen from the acquired image (step S12).

The control unit 51 extracts information regarding the monitor screen from the detected monitor screen (step S13), stores the extracted information in a measurement information DB 542 together with the imaging date and time (step S14), and ends the processing.

In the seventh embodiment, the detection result of the monitor screen is not stored and is directly used for the processing of extracting the measurement information, whereby the real-time performance for executing the processing in real time can be improved. In addition, it is not necessary to have a capacity for storing the detection result of the monitor screen, and thus, there is no concern about the capacity of the mass storage unit 54.

The technical features (components) described in the respective embodiments can be combined with each other, and new technical features can be formed by the combination.

It should be construed that the embodiments disclosed herein are illustrative in all respects and not restrictive. The scope of the present invention is indicated not by the above meaning but by the claims and is intended to include all changes within the meaning and scope equivalent to the claims.

REFERENCE SIGNS LIST

10, 11, 12 Imaging device
100 Operating room
1P Program
20, 21, 22 Measurement device
201, 211, 221 Monitor
50 Information processing device
51 Control unit

52 Communication unit
53 Storage unit
54 Mass storage unit
541 Image DB
542 Measurement information DB
55 Reading unit
56 Display unit
57 Operation unit
M Behavior recognition model

What is claimed is:

1. A method for managing a medical treatment using a plurality of medical devices coupled to a patient, wherein the medical devices have respective display devices each displaying respective medical information, the method comprising the steps of:

acquiring a surgical space image that is captured by an imaging device imaging a surgical space, wherein the surgical space image includes monitor screens of the respective display devices which are dispersedly located in the surgical space;

extracting information regarding measurement information displayed by the monitor screen of each of the display devices on the basis of the acquired surgical space image;

storing the extracted information of each of the display devices in time series to collectively manage the medical devices;

recognizing a blocking object present between one of the monitor screens and the imaging device; and extracting the information regarding the one of the monitor screens except for a region of the blocking object that has been recognized.

2. The method according to claim 1, wherein the extracted information is comprised of a measurement value, text data, graph data, or a medical image displayed on the monitor screen.

3. The method according to claim 1, further comprising the step of:

generating a trend graph using the extracted information.

4. The method according to claim 1, wherein the extracted information is comprised of a displayed measurement value from one of the medical devices, the method further comprising the steps of:

acquiring an actual measurement value from the one of the medical devices;

comparing the extracted information with the actual measurement value that has been acquired; and storing an image of the monitor screen from which the extracted information has been extracted together with an imaging date and time in association with the actual measurement value when a difference between the extracted information and the actual measurement value is equal to or greater than a predetermined threshold.

5. The method according to claim 4, further comprising the step of:

outputting a warning information to an operator in the medical environment when the difference between the extracted information and the actual measurement value is equal to or greater than the predetermined threshold.

6. The method according to claim 1, further comprising the steps of:

receiving a region coordinate corresponding to one of the monitor screens in the surgical space image; and extracting the information regarding measurement information displayed by the one of the monitor screens from the surgical space image in the region coordinate which has been received.

7. The method according to claim 1, further comprising the step of:

when an operator is recognized as the blocking object, specifying a position of the operator that has been recognized.

8. The method according to claim 1, further comprising the steps of:

extracting a plurality of types of measurement values displayed on one of the monitor screens;

determining whether or not an abnormality occurs in the patient on the basis of the plurality of types of measurement values that has been extracted; and outputting abnormality-related information when it is determined that the abnormality has occurred.

9. The method according to claim 8, further comprising the steps of:

outputting advice information for eliminating the abnormality, when it is determined that the abnormality has occurred.

10. The method according to claim 1, wherein the surgical space image captures an operator present in the surgical space, and wherein the method further comprises the steps of:

causing a model that is trained in such a manner as to output behavior information regarding a behavior of the operator when receiving the surgical space image as an input to receive the acquired surgical space image and output the behavior information of the operator; and storing the output behavior information of the operator and the extracted information regarding the monitor screen in association with each other in time series.

11. The method according to claim 10, further comprising the step of:

when an abnormality occurs in the extracted information regarding one of the monitor screens, identifying a type of the abnormality on the basis of the behavior information of the operator.

12. A method for managing a medical treatment using a plurality of medical devices coupled to a patient, wherein the medical devices have respective display devices each displaying respective medical information, the method comprising the steps of:

acquiring a surgical space image that is captured by an imaging device imaging a surgical space, wherein the surgical space image includes monitor screens of the respective display devices which are dispersedly located in the surgical space;

extracting information regarding measurement information displayed by the monitor screen of each of the display devices on the basis of the acquired surgical space image, wherein the extracted information is comprised of a displayed measurement value from one of the medical devices;

storing the extracted information of each of the display devices in time series to collectively manage the medical devices;

acquiring an actual measurement value from the one of the medical devices;

comparing the extracted information with the actual measurement value that has been acquired; and storing an image of the monitor screen from which the extracted information has been extracted together with an imaging date and time in association with the actual measurement value when a difference between the extracted information and the actual measurement value is equal to or greater than a predetermined threshold.

13. The method according to claim 12, further comprising the step of:

outputting a warning information to an operator in the medical environment when the difference between the extracted information and the actual measurement value is equal to or greater than the predetermined threshold.

14. A method for managing a medical treatment using a plurality of medical devices coupled to a patient, wherein the medical devices have respective display devices each displaying respective medical information, the method comprising the steps of:

acquiring a surgical space image that is captured by an imaging device imaging a surgical space, wherein the surgical space image includes monitor screens of the respective display devices which are dispersedly located in the surgical space;

extracting information regarding measurement information displayed by the monitor screen of each of the display devices on the basis of the acquired surgical space image;

storing the extracted information of each of the display devices in time series to collectively manage the medical devices; and wherein:

the imaging device includes a first imaging device and a second imaging device that are installed at different locations;

the surgical space image includes a first image captured by the first imaging device and a second image captured by the second imaging device; and the step of extracting information selectively uses the first image and the second image depending on the locations where the first imaging device and the second imaging device are installed, and a priority order of the first and second imaging devices regarding one of the monitor screens.

15. The method according to claim 14, wherein the first imaging device has a first priority and the second imaging device has a second priority for one of the monitor screens, the method further comprising the step of:

extracting the information regarding one of the monitor screens using the second image instead of the first image when a blocking object is recognized blocking the one of the monitor screens in the first image.

* * * * *